United States Patent
Scrafton et al.

(10) Patent No.: US 8,642,112 B2
(45) Date of Patent: Feb. 4, 2014

(54) THERMALLY TREATED CERAMIC COATING FOR IMPLANTS

(75) Inventors: Joel G. Scrafton, Syracuse, IN (US); Jeffrey P. Anderson, Warsaw, IN (US); David M. Miller, Warsaw, IN (US); Oludele O. Popoola, Granger, IN (US)

(73) Assignee: Zimmer, Inc., Warsaw, IN (US)

( * ) Notice: Subject to any disclaimer, the term of this patent is extended or adjusted under 35 U.S.C. 154(b) by 1208 days.

(21) Appl. No.: 12/503,535

(22) Filed: Jul. 15, 2009

(65) Prior Publication Data

US 2010/0016987 A1 Jan. 21, 2010

Related U.S. Application Data

(60) Provisional application No. 61/081,119, filed on Jul. 16, 2008.

(51) Int. Cl.
*A61L 33/00* (2006.01)

(52) U.S. Cl.
USPC ........... 427/2.24; 427/2.1; 427/294; 427/295; 427/412.1

(58) Field of Classification Search
USPC ..................... 623/18; 3/1.911, 1.91; 427/2.26
See application file for complete search history.

(56) References Cited

U.S. PATENT DOCUMENTS

| | | | |
|---|---|---|---|
| 3,989,872 A | 11/1976 | Ball | |
| 4,000,525 A * | 1/1977 | Klawitter et al. | 623/20.32 |
| 4,656,145 A | 4/1987 | Soroi | |
| 4,764,089 A | 8/1988 | Strangman | |
| 4,914,794 A | 4/1990 | Strangman | |
| 5,037,438 A * | 8/1991 | Davidson | 623/22.15 |
| 5,180,394 A | 1/1993 | Davidson | |
| 5,308,412 A | 5/1994 | Shetty et al. | |
| 5,372,660 A | 12/1994 | Davidson et al. | |
| 5,384,200 A | 1/1995 | Giles et al. | |
| 5,674,293 A | 10/1997 | Armini et al. | |
| 5,900,283 A | 5/1999 | Vakil et al. | |
| 5,980,974 A | 11/1999 | Armini et al. | |
| 5,993,976 A | 11/1999 | Sahoo et al. | |
| 6,585,772 B2 | 7/2003 | Hunter et al. | |
| 6,620,520 B2 | 9/2003 | O'Donnell et al. | |
| 6,685,987 B2 | 2/2004 | Shetty | |
| 6,869,550 B2 | 3/2005 | Dorfman et al. | |
| 6,893,994 B2 | 5/2005 | Wallar | |

(Continued)

FOREIGN PATENT DOCUMENTS

| | | | |
|---|---|---|---|
| EP | 1806155 A2 | 7/2007 | |
| EP | 1086155 | * 11/2007 | A61L 27/30 |

OTHER PUBLICATIONS

Written Opinion and International Search Report mailed Aug. 16, 2010 in related International Application No. PCT/US2009/050709.

(Continued)

*Primary Examiner* — Dah-Wei Yuan
*Assistant Examiner* — Andrew Bowman
(74) *Attorney, Agent, or Firm* — Schwegman, Lundberg & Woessner, P.A.

(57) ABSTRACT

A prosthetic implant having a thermally treated ceramic coating and a method of producing a coated prosthetic implant. The ceramic coating is deposited onto the prosthetic implant such as by a plasma spray coating process. The prosthetic implant is thermally treated in a low oxygen environment to increase the hardness and wear-resistance of the ceramic coating for improved articulation of the prosthetic implant.

20 Claims, 4 Drawing Sheets

(56) References Cited

U.S. PATENT DOCUMENTS

| | | |
|---|---|---|
| 6,945,448 B2 | 9/2005 | Medlin et al. |
| 7,182,784 B2 | 2/2007 | Evans et al. |
| 7,255,898 B2 | 8/2007 | O'Donnell et al. |
| 7,338,529 B1 | 3/2008 | Higgins |
| 7,473,278 B2 | 1/2009 | Hunter et al. |
| 2004/0002766 A1 | 1/2004 | Hunter et al. |
| 2006/0118035 A1 | 6/2006 | Lasater |
| 2006/0233944 A1 | 10/2006 | Popoola et al. |
| 2007/0078521 A1 | 4/2007 | Overholser et al. |
| 2008/0288081 A1 | 11/2008 | Scrafton et al. |
| 2009/0012611 A1 | 1/2009 | Brosnahan, III et al. |

OTHER PUBLICATIONS

Article "Ceramic Formation on Metallic Surfaces (Ceramization) for Medical Application," J. Rieu, Clinical Materials 12 (1993) pp. 227-235 Rieu.

Article "Microstructure and Erosion Resistance of Vacuum-plasma-sprayed Co—Ni—Cr—Al—Y/Al2O3 Composite Coatings," B. Gudmundsson et al., Materials Science and Engineering, A108 (1989), pp. 87-95 Gudmundsson.

Special 510(k) Premarket Notification, Columbus Total Knee System AS, May 2, 2007, 2 pages.

* cited by examiner

THERMALLY TREATED CERAMIC COATING FOR IMPLANTS

CROSS REFERENCE TO RELATED APPLICATION

This application claims priority from U.S. Provisional Patent Application No. 61/081,119, entitled "Black Zirconia Plasma Sprayed Coating," filed on Jul. 16, 2008 by the same inventors hereof, the disclosure of which is expressly incorporated herein by reference.

BACKGROUND

1. Field of the Invention

The present invention relates to prosthetic implants and, in particular, to prosthetic implants having a thermally treated ceramic coating and to a method of producing a coated prosthetic implant.

2. Description of the Related Art

Prosthetic implants are utilized to repair and/or replace damaged bone and tissue in the human body. For example, a prosthetic knee may be implanted to replace a damaged knee joint formed between a femur and a tibia. The prosthetic knee may include a femoral component and/or a tibial component.

The femoral component may be shaped to replicate one or both of the natural femoral condyles. One side of the femoral component is secured to a resected distal femur and the opposing side of the femoral component is configured to articulate against the tibial component or the natural tibia. The femoral component may be formed entirely of a rigid metal, such as a cobalt-chromium-molybdenum (CoCrMo) alloy, to withstand the load patterns of the knee joint.

The tibial component may include a tibial articulating component and a tibial tray component. The tibial articulating component may be concave in shape to receive natural or prosthetic femoral condyles. The tibial tray component is secured to a resected proximal tibia. The tibial articulating component may be formed of a polymer to facilitate articulation with the femoral component or the natural femur, while the tibial tray component may be formed of a metal to provide strength and rigidity to the tibial component of the prosthetic knee.

In use, the metallic femoral component may articulate against the polymeric tibial component to replicate the natural, anatomical articulation of the knee joint.

SUMMARY

The present invention provides a prosthetic implant having a thermally treated ceramic coating. The present invention also provides a method of producing a coated prosthetic implant. The ceramic coating is applied to the prosthetic implant such as by a plasma spray process. The prosthetic implant is thermally treated in a low oxygen environment to increase the hardness and wear-resistance of the ceramic coating for improved articulation of the prosthetic implant.

According to an embodiment of the present invention, a method is provided for producing a coated prosthetic implant. The method includes the steps of providing a substrate, depositing a ceramic material onto the substrate to provide a coated implant, the ceramic material defining an articulating surface of the coated implant, and after the depositing step, heating the coated implant to an elevated temperature sufficient to increase the hardness of the deposited ceramic material.

According to another embodiment of the present invention, a method is provided for producing a coated prosthetic implant. The method includes the steps of providing a substrate, depositing a ceramic material onto the substrate to provide a coated implant, the ceramic material defining an articulating surface of the coated implant, and heating the coated implant in a low oxygen environment.

According to yet another embodiment of the present invention, a method is provided for producing a coated prosthetic implant. The method includes the steps of providing a substrate, depositing a ceramic material onto the substrate to provide a coated implant, the ceramic material defining an articulating surface of the coated implant, and after the depositing step, heating the coated implant in a low oxygen environment to an elevated temperature sufficient to visibly darken the deposited ceramic material in color.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
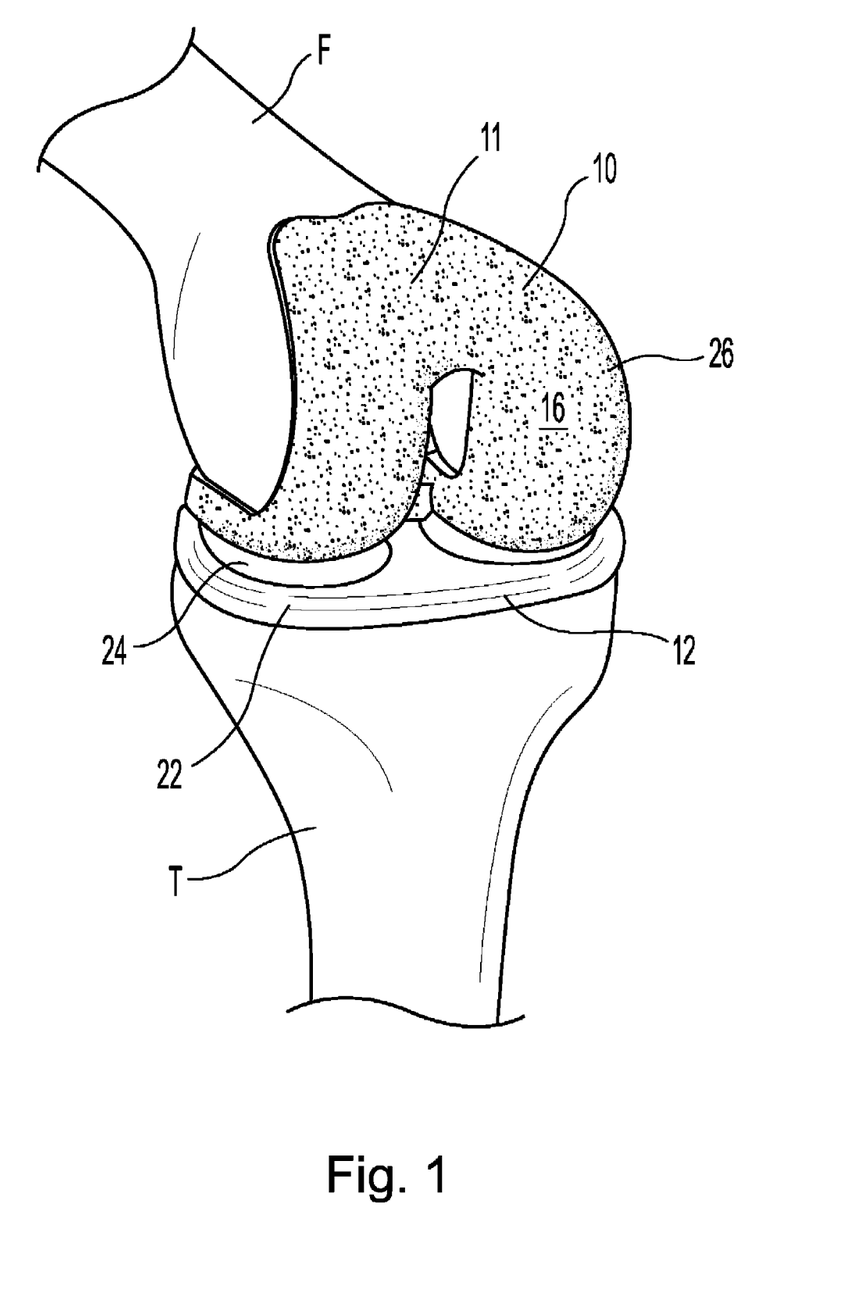
FIG. 1 is a perspective view of a prosthetic femoral component secured to a femur and a prosthetic tibial component secured to a tibia.

Referring to FIG. 1, a prosthetic implant is shown in the form of a prosthetic knee including femoral component 10 secured to femur F and tibial component 12 secured to tibia T. Although the prosthetic implant is described herein in the form of a prosthetic knee, the present invention is generally applicable to any prosthetic implant designed to articulate against a natural component of the body or an adjacent prosthetic implant, such as a prosthetic component of the hip joint, the shoulder joint, the elbow joint, or another joint.

Figure 2:
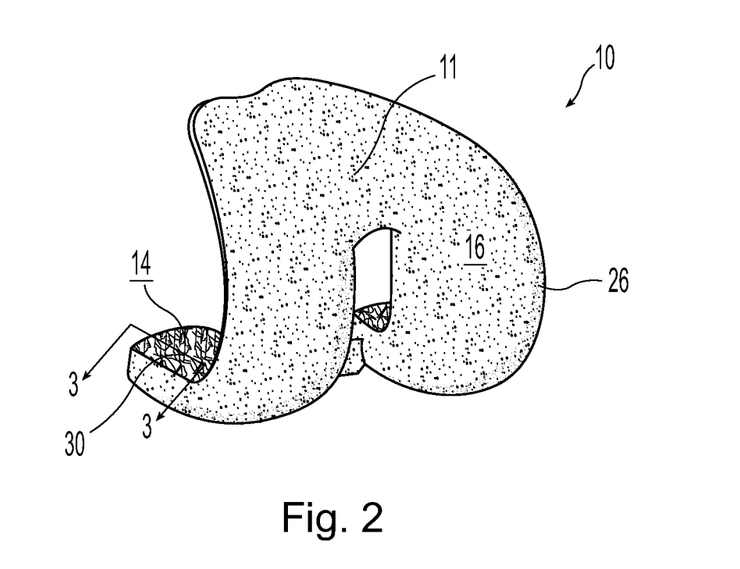
FIG. 2 is a perspective view of the prosthetic femoral component of FIG. 1.

Referring to FIGS. 1 and 2, femoral component 10 includes body 11, femoral attachment surface or non-articulating surface 14, and articulating surface 16. Femoral attachment surface 14 is secured to a prepared distal end of femur F. Articulating surface 16 is located opposite femoral attachment surface 14 and is configured to articulate against tibial component 12 or a natural tibia T. As illustrated, body 11 of femoral component 10 is shaped to replicate both of the natural condyles of femur F, but body 11 of femoral component 10 may also be formed as a unicondylar prosthesis having only a single condylar portion.

Body 11 of femoral component 10 may be formed of a rigid, biocompatible material capable of withstanding the load patterns of the knee joint. An exemplary body 11 of femoral component 10 may be formed of titanium, a titanium alloy, or another suitable material, for example. Advantageously, a prosthetic implant constructed of titanium or a titanium alloy may be biocompatible, durable, and lightweight and may resist corrosion. Alternatively, body 11 of femoral component 10 may be formed of cobalt chromium or a cobalt-chromium-molybdenum (CoCrMo) alloy, for example.

Referring again to FIG. 1, tibial component 12 includes tray component 22 and articulating component 24. Tray component 22 is secured to a prepared proximal end of tibia T. Articulating component 24 is attached to tray component 22 or is integrally formed with tray component 22 and is configured to articulate against femoral component 10 or a natural femur F. In use, articulating component 24 serves as a bearing layer to cushion the impact and reduce friction between femoral component 10 and tibial component 12.

Tray component 22 of tibial component 12 may be formed of a rigid, biocompatible material. For example, tray component 22 of tibial component 12 may be formed of titanium, a titanium alloy, cobalt chromium, a cobalt chromium molybdenum alloy, porous tantalum, a highly porous biomaterial, such as that described below, or another suitable material. Advantageously, a highly porous biomaterial is useful as a bone substitute and as cell and tissue receptive material, which may promote bone ingrowth from tibia T into tray component 22.

Articulating component 24 of tibial component 12 may be formed of a resilient, biocompatible material. For example, articulating component 24 of tibial component 12 may be formed of a polymer, including, but not limited to, a poly ether ether ketone (PEEK), fiber reinforced poly ether ether ketone, ultrahigh molecular weight polyethylene (UHMWPE), crosslinked ultrahigh molecular weight polyethylene, or polyether ketone ether ether ketone. Advantageously, by utilizing a resilient material for articulating component 24, wear between femoral component 10 and tibial component 12 may be reduced.

Figure 3:
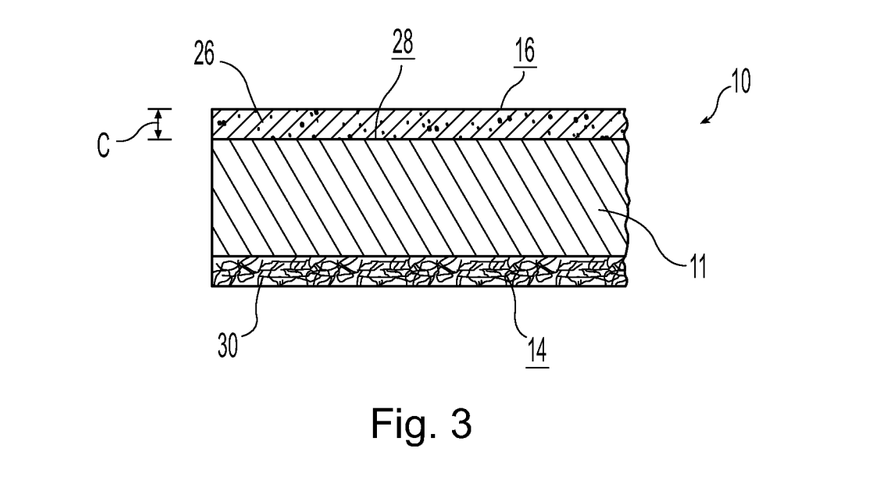
FIG. 3 is a partial cross-sectional view of the prosthetic femoral component of FIG. 2 taken along line 3-3 of FIG. 2.

Referring to FIGS. 1-3, to increase the hardness and wear-resistance of femoral component 10, coating 26 may be applied to femoral component 10. According to an exemplary embodiment of the present invention, coating 26 may be applied to at least the portion of femoral component 10 that will articulate against an adjacent surface after implantation, such as tibial component 12. Therefore, coating 26 may be applied to articulating surface 16 of femoral component 10. The surface of femoral component 10 coated with coating 26 is referred to herein as substrate 28.

According to an exemplary embodiment of the present invention, coating 26 may include a ceramic material. For example, coating 26 may include an oxide ceramic material, such as zirconia ($ZrO_2$) or alumina ($Al_2O_3$), a non-oxide ceramic material, such as silicon nitride ($Si_3N_4$) or silicon carbide (SiC), another ceramic material, or mixtures thereof. The ceramic material may be blended with a stabilizer. For example, the ceramic material may include yttria ($Y_2O_3$), magnesia (MgO), ceria ($CeO_2$), calcia (CaO), another known stabilizer, or mixtures thereof. An exemplary coating 26 includes tetragonal zirconia blended with approximately 8 mole percent yttria. An example of such a coating material is Yttria-Stabilized Zirconia generally available from Progressive Technologies of Grand Rapids, Mich.

Figure 4:
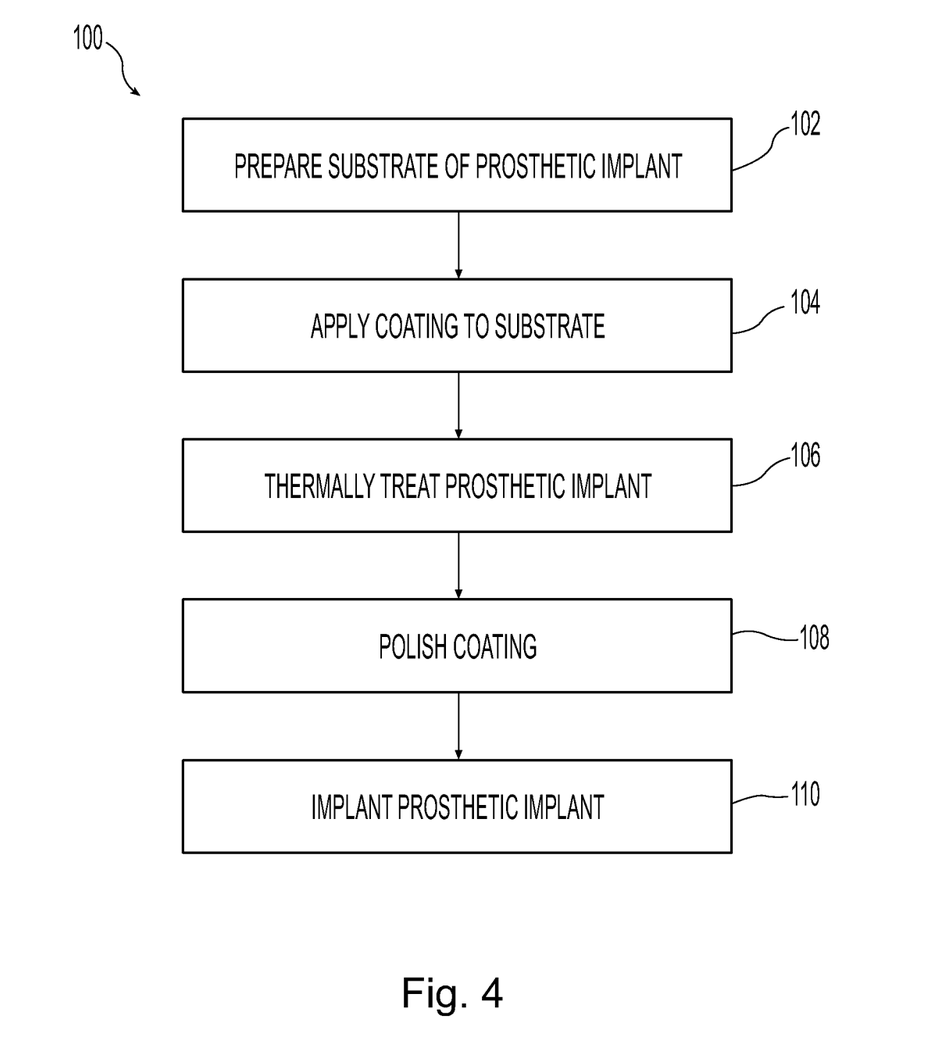
FIG. 4 is a flow diagram of an exemplary method of the present invention.

Referring next to FIG. 4, an exemplary method 100 of coating femoral component 10 with coating 26 is illustrated schematically. Beginning at step 102, substrate 28 of femoral component 10 is prepared to receive ceramic coating 26. Preparing substrate 28 may involve blasting substrate 28 with a blast media, such as aluminum oxide. Also, preparing substrate 28 may involve cleaning substrate 28 to remove dirt, residual blast media, and other substances that may affect the ability of ceramic coating 26 to adhere to substrate 28.

Continuing to step 104 of FIG. 4, ceramic coating 26 is applied to substrate 28 of femoral component 10. According to an exemplary embodiment of the present method, ceramic coating 26 is spray coated onto substrate 28 of femoral component 10. The spray coating process may include a plasma spray process, a high velocity oxygen fuel (HVOF) thermal spray process, an arc spray process, or another suitable spray coating process. Advantageously, spray coating processes may be carried out without increasing the temperature of substrate 28, thereby avoiding damage, metallurgical changes, and distortion of femoral component 10. Several exemplary spray coating processes are described below.

The plasma spray process involves providing a coating material in the form of a fine or ultra-fine powder, such as yttria-stabilized zirconia powder. The powdered coating material is injected into a high temperature plasma flame. The plasma flame rapidly heats and accelerates the coating material. The heated coating material impacts and splatters onto a cool substrate. After impact, the coating material quickly cools and hardens to form a coating layer on the substrate.

The HVOF thermal spray process involves providing a coating material in the form of a fine or ultra-fine powder, such as yttria-stabilized zirconia powder. The powdered coating material is fed into a chamber. Fuel, such as kerosene, acetylene, propylene or hydrogen, is also fed into the chamber along with oxygen. The fuel combusts into a flame, and the flame travels with increasing velocity through a nozzle extending from the chamber. The coating material is heated by the flame and carried out of the chamber through the nozzle until impacting the substrate. After impact, the coating material quickly cools and hardens to form a coating layer on the substrate.

The arc spray process involves using an electric arc to melt the coating material. The molten coating material is atomized by compressed air and propelled towards the substrate. After impact, the coating material quickly cools and hardens to form a coating layer on the substrate.

In addition to spray coating processes, ceramic coating 26 may also be applied to substrate 28 by laser cladding, ion beam assisted deposition (IBAD), chemical vapor deposition (CVD), physical vapor deposition (PVD), or other suitable processes.

Referring still to step 104 of FIG. 4, ceramic coating 26 should be applied to substrate 28 of femoral component 10 to provide a suitable layer of protection for femoral component 10. As shown in FIG. 3, ceramic coating 26 has thickness C. The various layers illustrated in FIG. 3 are not necessarily drawn to scale, and the illustrated scale is not intended to limit the scope of the present invention. After step 104, thickness C of ceramic coating 26 may be as small as approximately 0.005" (127 microns), 0.010" (254 microns), or 0.015" (381 microns) or as large as approximately 0.020" (508 microns), 0.025" (635 microns), 0.030" (762 microns), or more, for example.

Also, ceramic coating 26 should be applied to substrate 28 of femoral component 10 to maximize the smoothness and minimize the porosity of the coated surface. According to an exemplary embodiment of the present invention, after step 104, ceramic coating 26 may have a porosity below approximately 0.1%, 0.5%, or 1.0% by volume, for example.

Upon completion of step 104 of FIG. 4, ceramic coating 26 on femoral component 10 may be light in color. The color of ceramic coating 26 may depend on the coating material used to form ceramic coating 26 and the spray process used to apply ceramic coating 26. For example, when yttria-stabilized zirconia is plasma sprayed onto substrate 28, ceramic coating 26 of femoral component 10 may be beige, yellow, tan, gold, or a similar color.

Continuing to step 106 of FIG. 4, femoral component 10 having ceramic coating 26 is thermally treated in a low oxygen environment, such as a vacuum furnace or under a blanket of inert gas, to harden ceramic coating 26. Theoretically, at a temperature of 940° C., reduction of ceramic zirconia occurs at an oxygen partial pressure of about $1\times10^{-40}$ atmospheres (see for example C. H. P. Lupis, "Chemical Thermodynamics of Materials," North-Holland, N.Y., page 134, 1983). However, reduction of zirconia sufficient to cause the oxide color change has been demonstrated to occur at higher oxygen partial pressures (see Example). For example, a low oxygen environment may have oxygen present at a partial pressure as high as approximately $1\times10^{-9}$ atmospheres, $5\times10^{-9}$ atmospheres, $1\times10^{-8}$ atmospheres, or more. The thermal treatment conditions may vary depending on the desired result, such as the desired hardness of ceramic coating 26. For example, femoral component 10 having ceramic coating 26 may be heated in a vacuum furnace at a temperature as low as approximately 750° C. (1,382° F.), 800° C. (1,472° F.), 850° C. (1,562° F.), or 900° C. (1,652° F.) or as high as approximately 950° C. (1,742° F.), 1000° C. (1,832° F.), 1050° C. (1,922° F.), 1100° C. (2,012° F.), or more. At these temperatures, femoral component 10 may be thermally treated for as little as approximately 1 hour, 4 hours, 6 hours, 8 hours, 10 hours, or 12 hours or as long as approximately 14 hours, 16 hours, 18 hours, 20 hours, or more, for example.

While ceramic coating 26 is undergoing thermal treatment during step 104 (FIG. 4), porous layer 30 (FIGS. 1-3) may simultaneously be attached to body 11 of femoral component 10. Advantageously, porous layer 30 may be secured to femoral attachment surface 14 to enhance fixation between femoral component 10 and femur F by promoting bone ingrowth into porous layer 30. An exemplary method of securing porous layer 30 to a metallic body 11 of femoral component 10 at an elevated temperature via diffusion bonding is disclosed in U.S. Pat. No. 6,945,448, the disclosure of which is expressly incorporated herein by reference.

Porous layer 30 may be formed of a highly porous, open-cell biomaterial. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining the open cells therebetween, with each ligament generally including a carbon core covered by a thin film of metal such as tantalum, for example. The open cells between the ligaments form a matrix of continuous channels having no dead ends, such that growth of cancellous bone through the porous tantalum structure is uninhibited.

The porous tantalum may have a porosity as low as 55, 60, or 65 percent and as high as 80, 85, or 90 percent or more. Thus, porous tantalum is a lightweight, strong porous structure which is substantially uniform and consistent in composition, and closely resembles the structure of natural cancellous bone, thereby providing a matrix into which cancellous bone may grow to provide fixation of femoral component 10 to femur F.

The porous tantalum structure may be made in a variety of densities to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone to provide an improved matrix for bone ingrowth and mineralization.

Upon completion of step 106 of FIG. 4, ceramic coating 26 on femoral component 10 may be noticeably darker in color than it was when applied during step 104. The color of ceramic coating 26 may depend on the coating material used to form ceramic coating 26 and the spray process used to apply ceramic coating 26. Also, the color of ceramic coating 26 may depend on the thermal treatment conditions of step 106. For example, when yttria-stabilized zirconia is plasma sprayed onto substrate 28 and then heated in a vacuum furnace for approximately 16 hours at a temperature of approximately 940° C. (1,724° F.), ceramic coating 26 may turn to a dark color, such as brown, bronze, blue, gray black, or a similar color.

In addition to noticeably changing color after step 106, ceramic coating 26 on femoral component 10 may undergo measurable physical changes. Advantageously, ceramic coating 26 on femoral component 10 may increase in hardness. For example, the hardness of ceramic coating 26 may increase by approximately 10%, 20%, 30%, 40%, 50%, or more (See Example, Table 1). Also advantageously, the adhesion strength between ceramic coating 26 and substrate 28 may increase. For example, the hardness of ceramic coating 26 may increase by approximately 1%, 2%, 3%, 4%, 5%, 10%, or more (See Example, Table 2).

It is within the scope of the present invention that thermal treatment step 106 may cause ceramic coating 26 to transition to a more stable crystalline phase. For example, if zirconia is initially present in the tetragonal phase, thermal treatment step 106 may transition the zirconia to its monoclinic phase upon subsequent cooling. The crystalline phase of ceramic coating 26 may also be controlled with a stabilizer, such as yttria.

Thermally treating ceramic coating 26 on femoral component 10 may also increase the porosity of ceramic coating 26. Although too much porosity could cause femoral component 10 to wear against tibial component 12 (FIG. 1), some porosity may be advantageous in trapping lubricants between the articulating femoral component 10 and tibial component 12. After step 106, ceramic coating 26 may have a porosity below approximately 1.0%, 2.0%, or 3.0% by volume, for example. The increased porosity may be caused by vaporization of the stabilizer. By minimizing the porosity of ceramic coating 26 applied during step 104, the porosity of ceramic coating 26 after step 106 may also be minimized. According to an exemplary embodiment of the present invention, even after step 106, ceramic coating 26 may still have a porosity below approximately 1.0% by volume.

Continuing to step 108 of FIG. 4, femoral component 10 having ceramic coating 26 is polished to provide a smooth surface for articulation with tibial component 12 (FIG. 1). Femoral component 10 may be polished by any suitable ceramic polishing method known in the art, such as sphere grinding. Referring to FIG. 3, polishing may reduce thickness C of ceramic coating 26. In fact, polishing may remove a majority of ceramic coating 26 applied during step 104. After step 108, thickness C of ceramic coating 26 may be as small as approximately 0.001" (25 microns), 0.003" (76 microns), or 0.005" (127 microns) or as large as approximately 0.010" (254 microns), 0.013" (330 microns), 0.015" (381 microns), or more, for example.

Continuing to step 110 of FIG. 4, femoral component 10 having ceramic coating 26 is implanted into the body of a patient. As shown in FIG. 1, femoral attachment surface 14 is secured to a prepared distal end of femur F. Articulating surface 16 is configured to articulate against tibial component 12 or a natural tibia T.

Method 100 described above provides several advantages over current processes in which a ceramic surface layer is chemically grown onto a metal substrate. For example, in one known process, a zirconia surface layer is chemically grown onto a zirconium substrate by heating the substrate in an oxygen-rich environment. Some of these advantages are set forth below.

First, the coating process is faster than the chemical growth process. For example, a metal substrate may be spray coated in a few minutes, but may require several hours to chemically grow an adequate ceramic surface layer.

Second, the coating process may produce a thicker ceramic surface layer than the chemical growth process. For example, and as discussed above, a metal substrate may be spray coated with a ceramic surface layer between approximately 0.005" (127 microns) and 0.030" (762 microns) thick, or more, whereas reacted ceramic surface layers may grow up to 0.0008" (20 microns) thick. The increased thickness of the coated ceramic surface layer reduces the potential of wearing through the surface layer over time and exposing the metal substrate beneath. Also, the thickness of the coated ceramic surface layer accommodates finishing processes to smooth the surface layer, such as polishing step 108 of method 100. Such finishing processes would sacrifice a significant portion of the already thin, reacted ceramic surface layer.

Next, the coating process provides more flexibility in selecting the metal substrate than the chemical growth process. For example, growing a zirconia surface layer necessitates use of a zirconium substrate, whereas spray coating a zirconia surface layer accommodates titanium substrates, cobalt chromium substrates, cobalt-chromium-molybdenum (CoCrMo) substrates, and other suitable substrates. Therefore, the composition of the substrate is not dictated by the composition of the surface layer. Rather, the substrate may be selected based on hardness, biocompatibility, availability, cost, and other factors.

Finally, masking certain portions of the metal substrate from the ceramic surface layer is more easily accomplished during the coating process than the chemical growth process. For example, during the spray coating process, a portion of the metal substrate may be covered with a suitable shield to block liquid ceramic droplets. However, during the chemical growth process, the metal substrate must be covered with a suitable shield to block exposure to small, reactant gas particles.

EXAMPLE

Five prosthetic femoral components made of titanium were plasma spray coated with 8 mole percent yttria-stabilized zirconia and then heated in a vacuum furnace for approximately 8 hours at a temperature of approximately 940° C. (1,724° F.). The vacuum level was nominally $2.6 \times 10^{-5}$ torr ($3.4 \times 10^{-8}$ atmospheres). The oxygen partial pressure was estimated to be $5.2 \times 10^{-6}$ torr ($6.8 \times 10^{-9}$ atmospheres).

Figure 5:
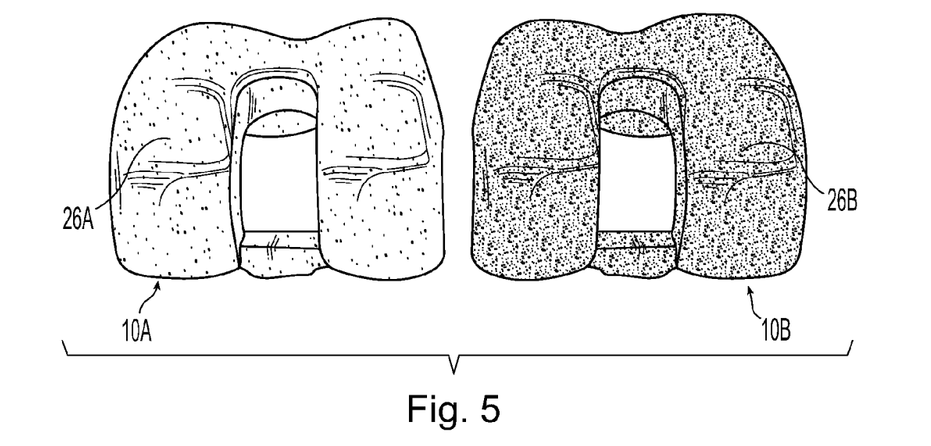
FIG. 5 is a perspective view of a first coated femoral component prior to thermal treatment and a second coated femoral component after thermal treatment.

As mentioned above, the ceramic coatings became noticeably darker in color after heating. This color change is schematically illustrated in FIG. 5 between an untreated femoral component 10A having tan-colored ceramic coating 26A and a thermally treated femoral component 10B having a black-colored ceramic coating 26B.

In addition to undergoing a noticeable color change, the ceramic coatings increased in hardness after heating. Knoop hardness ($H_K$) measurements were taken of the five samples before and after heating using standard Knoop hardness test methods. These measurements were averaged, and the results are set forth in Table 1 below. The average hardness of the ceramic coatings increased by approximately 42% after heating.

TABLE 1

| Condition | Average Hardness ($H_K$) |
|---|---|
| Before Thermal Treatment | 972 |
| After Thermal Treatment | 1377 |

Also, the adhesion strength between the ceramic coatings and the substrates increased after heating. Adhesion strength measurements were taken of five samples before and after heating. Adhesion strength was measured by pulling the ceramic coating away from the substrate using a tensile machine and measuring the force at which the ceramic coating broke away from the substrate. These measurements were averaged, and the results are set forth in Table 2 below. The average adhesion strength between the ceramic coatings and the substrates increased by approximately 2% after heating.

TABLE 2

| Condition | Average Adhesion Strength (psi) |
|---|---|
| Before Thermal Treatment | 5340 |
| After Thermal Treatment | 5440 |

Figure 6:
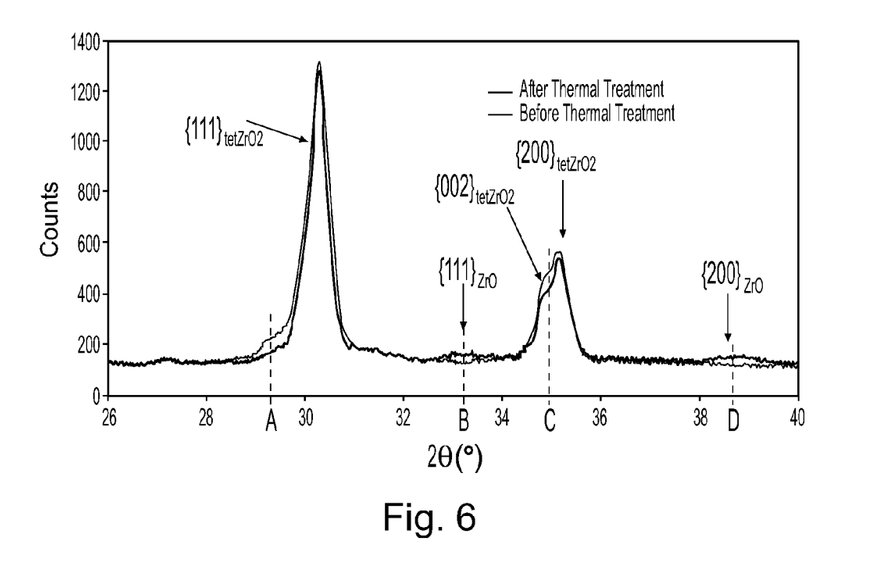
FIG. 6 is a graphical representation of an X-ray diffraction analysis performed on a sample coating of the present invention.

Referring to FIG. 6, X-ray diffraction was performed to analyze a sample ceramic coating before and after heating. Before heating, peaks located at approximately 30° and 35° indicated the presence of tetragonal zirconia ($ZrO_2$) in the ceramic coating. After heating, portions of the $ZrO_2$ peaks decreased in magnitude, such as near approximately 29° (point A) and 35° (point C). Also after heating, new peaks developed at approximately 33° (point B) and 39° (point D) that may indicate reduction of some $ZrO_2$ to $ZrO_{x<2}$ in the ceramic coating. The zirconium atoms may lose oxygen atoms to the surrounding low-oxygen environment, for example.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of producing a coated prosthetic implant, the method comprising:

providing a substrate;

depositing a ceramic material onto the substrate to provide a coated implant, the ceramic material defining an articulating surface of the coated implant;

after depositing the ceramic material, heating the coated implant to an elevated temperature to increase the hardness of the deposited ceramic material; and increasing porosity of the ceramic material by vaporization.

2. The method of claim 1, wherein heating comprises heating the coated implant to the elevated temperature of at least approximately 750° C.

3. The method of claim 1, wherein heating comprises heating the coated implant in a low oxygen environment.

4. The method of claim 1, wherein the substrate comprises one of titanium, a titanium alloy, a cobalt-chromium alloy, and a cobalt-chromium-molybdenum alloy.

5. The method of claim 1, wherein the ceramic material comprises at least one of zirconia, alumina, silicon nitride, and silicon carbide.

6. The method of claim 1, wherein increasing the porosity comprises vaporizing a stabilizer of the ceramic material, the stabilizer selected from the group consisting of yttria, magnesia, ceria, and calcia.

7. The method of claim 1, wherein depositing comprises at least one of plasma spraying, high velocity oxygen fuel thermal spraying, thermal spraying, arc spraying, laser cladding, ion beam assisted deposition, chemical vapor deposition, and physical vapor deposition.

8. The method of claim 1, wherein depositing comprises depositing the ceramic material onto the substrate at a thickness of more than approximately 0.001 inches.

9. The method of claim 1, wherein heating comprises increasing the hardness of the deposited ceramic material by more than approximately 10%.

10. A method of producing a coated prosthetic implant, the method comprising:

providing a substrate;

depositing a ceramic material including a stabilizer onto the substrate to provide a coated implant, the ceramic material defining an articulating surface of the coated implant;

heating the coated implant in a low oxygen environment; and vaporizing the stabilizer to increase porosity of the ceramic material.

11. The method of claim 10, wherein heating comprises heating the coated implant in a vacuum furnace.

12. The method of claim 10, wherein depositing comprises depositing the ceramic material onto the substrate at a thickness of more than approximately 0.001 inches.

13. The method of claim 10, wherein depositing comprises depositing the ceramic material onto the substrate at a thickness of more than approximately 0.005 inches.

14. A method of producing a coated prosthetic implant, the method comprising:

providing a substrate;

depositing a ceramic material including a stabilizer onto the substrate to provide a coated implant, the ceramic material defining an articulating surface of the coated implant, wherein porosity of the ceramic material is below about 1.0% by volume;

after depositing the ceramic material, heating the coated implant in a low oxygen environment to an elevated temperature to visibly darken the deposited ceramic material in color; and vaporizing the stabilizer to increase the porosity of the ceramic material to greater than about 1.0% by volume.

15. The method of claim 14, wherein heating comprises heating the coated implant in a vacuum furnace.

16. The method of claim 14, wherein heating comprises heating the coated implant to the elevated temperature of at least approximately 750° C.

17. The method of claim 14, wherein heating comprises darkening the deposited ceramic material from one of beige, yellow, tan, and gold to one of brown, bronze, blue, and gray black.

18. The method of claim 14, wherein depositing comprises depositing the ceramic material onto the substrate at a thickness of more than approximately 0.001 inches.

19. The method of claim 10, wherein vaporizing the stabilizer includes maintaining the porosity of the ceramic material below about 3.0% by volume.

20. The method of claim 10, wherein vaporizing the stabilizer includes increasing the porosity of the ceramic material from less than about 1.0% by volume to between about 1.0% by volume and about 3.0% by volume.

* * * * *